United States Patent [19]

Orlando et al.

[11] 3,989,570

[45] Nov. 2, 1976

[54] METHOD FOR PRODUCING AN IMPRINTING DEVICE

[75] Inventors: Joseph M. Orlando, Parsippany; Harry S. Katz, West Orange; Jack W. Rainford, Closter, all of N.J.

[73] Assignee: Precision Dynamics Corporation, Burbank, Calif.

[22] Filed: Sept. 5, 1974

[21] Appl. No.: 503,263

Related U.S. Application Data

[60] Division of Ser. No. 385,659, Aug. 6, 1973, Pat. No. 3,867,164, which is a continuation of Ser. No. 225,648, Feb. 11, 1972, abandoned, which is a continuation of Ser. No. 854,700, Sept. 2, 1969, abandoned.

[52] U.S. Cl. .............................. 156/239; 156/240; 156/277; 356/71; 427/1; 427/152
[51] Int. Cl.² .................... B32B 27/40; B32B 7/00; B32B 27/20
[58] Field of Search ............ 117/.5, 1.5, 36.1, 36.2, 117/3.1; 118/31.5; 283/7; 156/249, 277, 238–241; 356/71, 168; 427/1, 146, 152

[56] References Cited

UNITED STATES PATENTS

| | | | |
|---|---|---|---|
| 1,775,794 | 9/1930 | White | 356/71 |
| 2,313,807 | 3/1943 | Curry | 117/.5 |
| 3,227,474 | 1/1966 | Hoeflinger | 283/7 |
| 3,415,790 | 12/1968 | Davis et al. | 260/77.5 SP |
| 3,485,903 | 12/1969 | Findlay et al. | 117/36.1 X |
| 3,531,312 | 9/1970 | Newman | 117/36.1 X |
| 3,584,958 | 6/1971 | Miller et al. | 356/71 |

*Primary Examiner*—William A. Powell
*Assistant Examiner*—Thomas Bokan
*Attorney, Agent, or Firm*—Mahoney, Schick & Cislo

[57] ABSTRACT

A method of producing an imprinting device having a supporting member and an impression conforming film thereon comprising depositing a thin, conformable elastomeric coating on a web from a mixture of resinous elastomer, filler and liquid solvent, drying the coating to form a film; applying a coating of wet ink on one surface of the film and bonding the film to the supporting member and the method of producing the thin flat conformable film.

6 Claims, 5 Drawing Figures

METHOD FOR PRODUCING AN IMPRINTING DEVICE

RELATED APPLICATION

The present application discloses an improvement of an imprinting device disclosed in a commonly assigned and co-pending application Ser. No. 759,698 filed Sept. 13, 1968 and entitled "Identification System" and now issued U.S. Pat. No. 3,584,953. This application is a divisional application of application Ser. No. 385,659 filed Aug. 6, 1973 now issued U.S. Pat. No. 3,867,164 which, in turn, is a continuation of application Ser. No. 225,648 filed Feb. 11, 1972 now abandoned and which, in turn, is a continuation of U.S. patent application Ser. No. 854,700 filed Sept. 2, 1969 now abandoned.

BACKGROUND OF THE INVENTION

The above-mentioned U.S. Pat. No. 3,584,958 discloses an identification system which in one embodiment employs an imprinting device in the form of a recording card for taking fingerprints without applying any ink directly to the finger. This system has the obvious advantage of cleanliness over conventional fingerprint techniques. The recording card includes, in general, a frame member which is provided with at least one window therein, a thin sheet of impression conforming material secured across the frame window, inking means disposed on one surface of the sheet material, and a fingerprint receiving surface disposed on the inked side of the sheet material in alignment with the window. The fingerprint receiving surface is normally maintained in spaced relationship with the inking means. To take a print with the structure of the recording card disposed in the above-mentioned application, the individual's finger is placed on the side of the sheet material opposite to the side which carries the inking means. The sheet material is thereby stretched and caused to conform to the individual's fingerprint. In this condition, contact between the opposite inked surface of the impression conforming sheet material and the fingerprint receiving surface produces a clear and accurate ink reproduction of the fingerprint.

With the recording card disclosed in the above mentioned application, there are certain features which may present problems in particular applications unless the card is handled and used properly. One problem relates to the relationship between the inking means and the impression conforming sheet. As disclosed in said co-pending application, the inking means may include a coating of wet ink adhered to the surface of the impression conforming sheet, however, the uniformness of this coating and the strength of the adhesive bond formed between the wet ink coating and impression conforming sheet has been found to be less than desirable in some instances. For example, an uneven ink coating is apt to produce a print in which some of the lines are heavy and dark while others are rather faint and, in some instances imperceptible. A weak adhesive bond between the ink coating and the impression conforming sheet is apt to produce slippage at the interface between the ink and the sheet resulting in a smudged or blurred print in which the lines of the print are virtually indistinguishable from one another. Of course, a good quality print can be obtained with the recording card disclosed in said co-pending application if the user is careful to apply just the right amount of pressure when taking the print being especially careful to see that the inked surface of the impression conforming sheet and the print receiving surface are held in firmly and immovably together.

Another problem associated with the recording card disclosed in said co-pending application arises from the fact that the presence of the ink coating makes it impossible to see through the impression conforming sheet for purposes of determining in advance the precise location of the ultimate print on the print receiving surface. In certain applications, however the precise placement of the print on the print receiving surface is important. For example, where the print receiving surface consists of a standard form blank having one or more ruled boxes each of which is separately identified as containing a specified print, it is very important that the specified print be confined within the boundaries of the box designated for such purpose. A common example of such a standard form is the standard fingerprint blank used by law enforcement agencies. Such forms are generally provided with a series of ruled boxes identified as containing the print of a particular finger such as the thumb, forefinger, index finger and so forth. Of course, the print could be properly positioned on this type of standard form by using the recording card disclosed in the above-mentioned application if the user makes a careful estimation of the location of the proper box in relation to the surface area of the opaque impression conforming sheet.

SUMMARY OF THE INVENTION

In accordance with the teachings of the present invention, there is provided a method for providing an improved imprinting device for use with a print receiving surface which defines predetermined print receiving areas each of which is designated to contain a particular print.

In construction, the imprinting device includes generally a frame member having a window therein, a thin film of impression conforming material secured across the window of the frame member, and a coating of wet ink adhered to one surface of the film. But for the presence of the wet ink, the film of impression conforming material is substantially transparent. The ink coating, however, renders the film opaque.

Since the recording card of the present invention is intended for making an ink print within one of the predetermined print receiving areas on the print receiving surface, means are provided for visually dividing the opaque film into sections corresponding in location to the location of the print receiving areas on the print receiving surface. This means includes a clear uninked portion of the film which overlies the window in the frame member so that at least a portion of the boundary lines dividing the print receiving areas is exposed to view. With this arrangement, the location of a particular print receiving area may be easily and accurately estimated simply by drawing imaginary extensions of the boundary line portions exposed to view through the ink free portion of the film.

The subject matter of the present invention is directed particularly to the formulation and method of making the film of impression conforming material and also to the method of making the recording card employing the film having the formulation disclosed herein.

The method by which the film is formed in the present invention comprises depositing a thin resinous coating containing a specially formulated resinous elastomer in a liquid solvent upon a web, drying the resinous coating to form a film, applying a wet ink coating to the exposed surface of the web supported film, and finally removing the film from the web. The liquid solvent is volatilized during the drying operation leaving a thin extremely smooth film having excellent ink retention characteristics. Moreover, the smoothness of the film results in an even coating of ink and, hence, a print obtained by using the imprinting device of the present invention which employs this film is clear and accurate with no smudged or blurred spots.

DETAILED DESCRIPTION OF THE INVENTION

At the outset, it should be pointed out that, in addition to the specific art of fingerprinting, the imprinting device of the present invention is susceptible of general application in the graphic arts field where it is desired to take the print of a given reference surface. For instance, the imprinting device of the present invention is readily adapted for medical identification purposes in hospitals and the like (e.g., infants footprints) or, by way of further example, the imprinting device of the invention may be advantageously used as an artist's tool in the creation of artistic paintings. However, for the purpose of clear and accurate description and ready understanding of the inventive concept underlying the present invention, reference will be quite frequently made to the art of fingerprinting as the description of the imprinting device proceeds.

Figure 1:
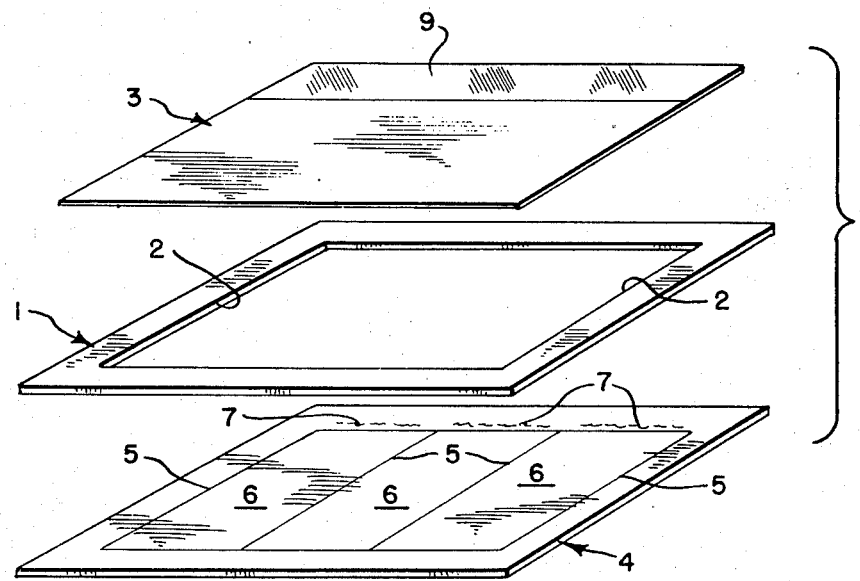
FIG. 1 is an exploded view of the recording card of this invention.
Figure 2:
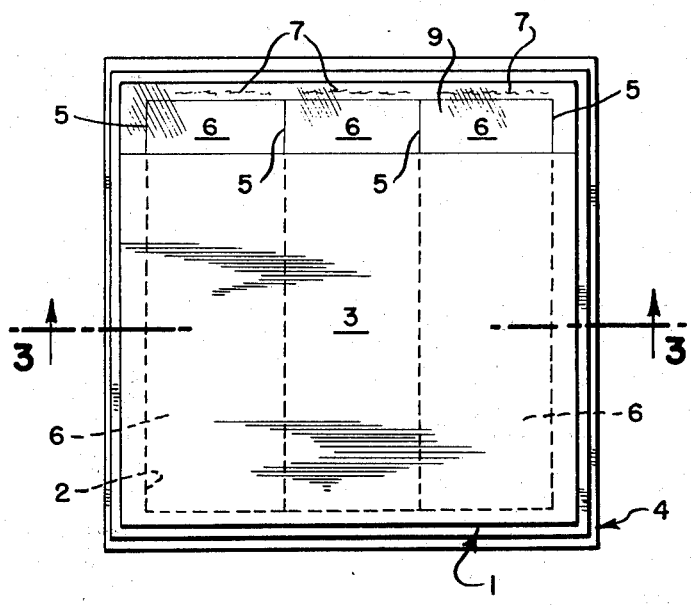
FIG. 2 is a top plan view, in assembled condition, of the recording card shown in FIG. 1.
Figure 3:
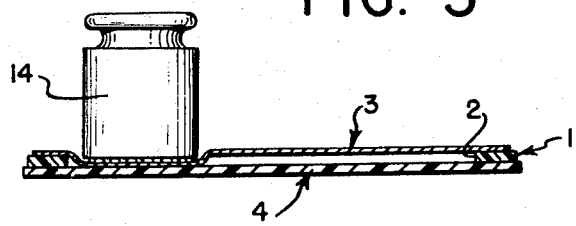
FIG. 3 is a cross-sectional view taken along the lines 3—3 of FIG. 2.

With reference to FIGS. 1 to 3, the imprinting device of the present invention includes generally a frame member 1 having a window 2, a thin film 3 of impression conforming material secured across the window 2, and a wet ink coating disposed on the surface of the film facing through the window in frame member 1. Thus, as shown in FIG. 3, the frame member supports the inked surface of the film 3 spaced from the print receiving surface 4 on which the print of reference surface 14 is to be placed.

The frame member may be made of cardboard, plastic or any other suitable material having a thickness of about 1/16 of an inch and the film 3 is impression conforming in the sense that it is thin enough and flexible enough to conform precisely to the impressions and ridges defining the particular reference surface to be printed. As will be more fully described hereinafter, a suitable material for the film is a polyurethane sheet having a thickness of about 0.0001 to 0.001 inches.

The print receiving surface 4 has a series of ruled lines 5 which define predetermined print receiving areas 6. Each print receiving area may be provided with an appropriate caption or legend 7 inscribed at the foot thereof for the purpose of identifying the particular print contained therein. The print receiving surface usually comprises a standard form blank; for instance, the standard form blank commonly used by law enforcement agencies for the purpose of recording and classifying the fingerprints of a particular individual. In such an application, the reference surface would consist of an individual's finger and each print receiving area would designate the print of a particular finger such as the forefinger, thumb, index finger and so forth.

It will be recognized that presence of the wet ink coating means renders the portion of the normally transparent film it covers opaque thus concealing the location of the print receiving areas from view. Thus, in order to readily ascertain the location of the print receiving areas means are provided for visually dividing the recording card into sections located in accordance with the layout of the print receiving areas 6.

As shown in FIGS. 1 and 2, this means comprises a transparent portion 9 in the sheet material 3 overlying the window in body member 1. The transparent portion 9 is formed by leaving the margin along one side of the sheet material void of ink so that portions of boundary lines 5 of the print receiving areas 6 are exposed to view through the window 2 in body member 1. The width of the transparent margin must be such that it extends over the window 2 in body member 1 a sufficient distance to expose at least some portion of the boundary lines 5 of the underlying print receiving areas 6 clearly to view. As shown in FIG. 2 additional width may advantageously be allowed to also expose the captions 7 identifying each print receiving area.

With this arrangement the general location of each print receiving area may be accurately estimated by visual inspection. When a print is to be taken, the reference surface 14 is merely placed beneath the appropriate legend in between imaginary extensions of boundary lines 5 and pressed against the inked portion of the impression conforming sheet material to move its inked surface into contact with the designated print receiving area 6 on the print receiving surface 4.

Figure 4:
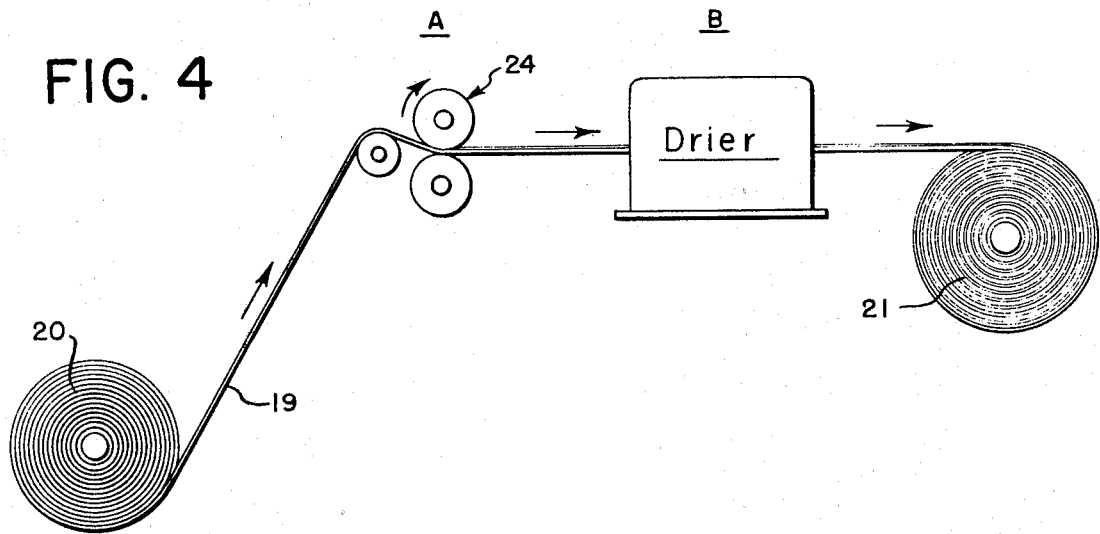
FIGS. 4 and 5 are diagrammatic illustrations of suitable apparatus for practicing the method of the present invention.
Figure 5:
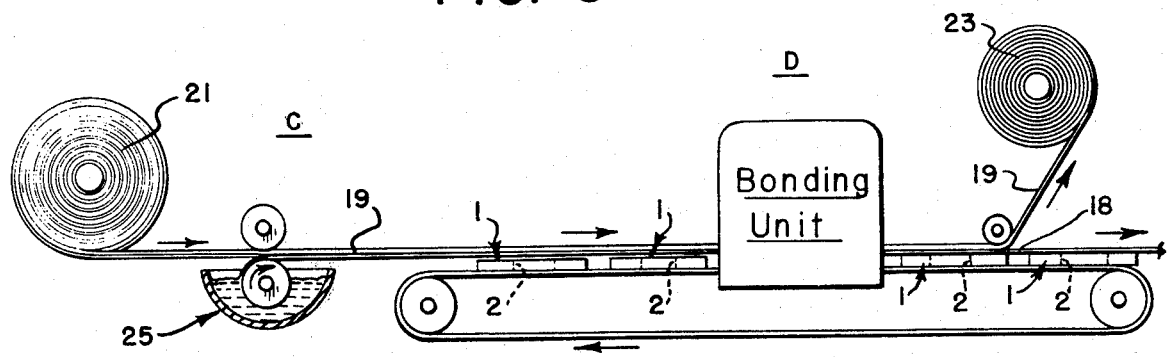

Referring now to FIGS. 4 and 5, the apparatus shown is divided into (1) a web charging zone A, (2) a drying zone B, (3) an ink coating zone C, and (4) a bonding zone D.

As will be explained in more detail below, the web 19 is unwound from a suitable supply spool 20 and passed first through the web charging zone A where a thin coating of resinous film forming material is deposited on its upper surface, then through the drying zone B where the resinous coating is dried by hot air to form a film and, eventually onto a suitable take-up spool 21.

When the take-up spool is sufficiently full, the web with the supported film is severed and the take-up spool is unwound in a direction opposite to the direction it was initially wound. As shown in FIG. 5, the film 21 is now disposed on the underside of the web 19. In this position, the web is directed through the ink coating zone C where a coating of wet ink is applied to the exposed surface of the web supported film. For the purpose described above, the ink is applied so as to leave a margin along one side of the film free of ink.

The web supported inked film is finally fed into the bonding zone D where the film is positioned over a plurality of frame member 1 with the inked surface of the film facing through the windows 2 in each frame member. The film while still on the web is bonded to the frame member by any suitable means. For instance, if the frame members are made of cardboard the film may be secured thereto by means of a suitable adhesive such as methyl-ethyl ketone base adhesive. Alternatively, if the frame members are made of plastic the bonding may be effected by applying heat to the edges of the film overlying the frame member to thereby fuse the frame and film together.

After the bonding operation is concluded, the web is stripped away from the film and wound on a suitable spool 23 to be later discarded. The frame members are then separated by severing the film portions 18 linking the individual frame members together, trimmed to remove any film overhanging the edges of the frame members and packaged in suitable containers for shipment to the user.

THE RESINOUS FILM FORMING MATERIAL

The resinous film forming material which is deposited on the web in the form of a thin coating comprises a resinous elastomer such as polyurethane and a filler such as diatomaceous earth in a liquid solvent carrier. This material is prepared by mixing an organic solvent with a suitable diluent to form the liquid solvent carrier. To this carrier is added a resinous elastomer in an amount ranging between about 5 to 50 parts per hundred parts by weight of the solvent carrier; the optimum amount being 15 parts resinous elastomer per 100 parts by weight of the solvent carrier. The liquid solvent carrier comprises 3 parts organic solent to 1 part diluent by weight. By preference the organic solvent is tetrahydrofuran (THF); the diluent is acetone; and the polyurethane is Estane Urethane Chip No. 570 manufactured by the B. F. Goodrich Corporation.

This mixture is introduced into a suitable comminution unit, such as a Ball mill, until such time as the resinous elastomer has been brought into solution. For instance, when using a Ball mill having an 11 to 12 inch diameter drum and carburundum as the grinding media, a time of about 8 to 12 hours at 45–55 r.p.m. is sufficient.

To the solution so formed is added diatomaceous earth in the amount of about 5 to 40 parts per hundred parts by weight of the resinous elastomer. In the preferred embodiment, the diatomaceous earth is "Celite 499" manufactured by the Johns-Manville Corporation which is added to the solution in the amount of 10 parts per hundred parts by weight of the resinous elastomer.

This mixture is then resubjected to the action of the Ball mill for a sufficient time to fully disperse the diatomaceous earth uniformly throughout the mixture, usually for about 20 hours.

The liquid solvent carrier is volatilized during the drying operation leaving a thin pliable film having a thickness such that the film is impression conforming in the sense defined above. A film thickness of about 0.0001 to 0.001 inches has been found to be most satisfactory.

This dispersion while free-flowing has a viscosity conductive to depositing a thin coating on the web having a thickness which remains substantially intact during the drying operation. The precise viscosity range for the dispersion is determined primarily by the particular device used for applying it to the web in the charging zone A. For instance, as shown in FIG. 4 a reverse roller type applicator 24 of conventional construction is provided for this purpose. With this device a viscosity ranging between 125 to 150 centipoises has been found to produce the best results. The viscosity is, of course, adjusted by providing the proper amount of solvent. The coating may alternatively be applied to the web by a conventional blade coater of the adjustable type at a blade setting which produces a film thickness of 0.00015 to 0.00025 inches. A suitable blade coater is the adjustable blade coater produced by the Boston Bradley Co.

THE INK COATING

The ink coating is applied to the exposed surface of the web supported film by means of a rotary Gravure Press, indicated diagrammatically at 25 in FIG. 5, using an inking cylinder 26 having 250 rulings per inch. Such presses are well known in the art and therefore in the interests of brevity further elaboration will be omitted.

The ink coating itself, for example, comprises a solution containing 4 parts of straight ink produced in accordance with formula 8A-7070 set forth in the specifications published by the Cilco Co. diluted with 1½ parts solvent, such as V. M. & P. naphtha. The ink coating when applied to the film remains wet in the sense that it is moist and slow drying but not wet enought to disturb the quality of the print. It will be obvious to those familiar with ink formulations, that other non-drying inks may be used.

THE WEB

A suitable web for practicing the above-described process consists of release paper such as clay coated bleached paper having an outer layer of high gloss smooth lacquer. Such a paper is produced by S. D. Warren Co., catalogue number AV C1S.

The film produced in accordance with teachings of the present invention has unusually good ink retention characteristics. That is, the adhesive bond between the wet ink coating and the impression conforming film is quite strong. This characteristic is attributed primarily to the presence of the uniform dispersion of diatomaceous earth which advantageously acts to absorb some of the liquid vehicle in which the ink is carried. Also, the diatomaceous earth modifies the surface energy of the film so that the ink wets better and adheres more strongly. While the diatomaceous earth imparts a milky color to the film, the film is still transparent enough to see clearly through any portions thereof which are not coated with ink.

The diatomaceous earth also acts as a flattening agent thereby rendering the surface of the film extremely smooth and even with considerably less irregularities than was previously the case with the impression conforming sheet material used with the recording card disclosed in said co-pending applicaton. The smoothness of the film surface, in turn, permits the ink coating to be applied more uniformly and hence the possibility of obtaining prints which vary in intensity and clearness is advantageously reduced.

The above description of the present invention has been made with reference to the preferred embodiment; however, it is to be understood that various changes may be made thereto without departing from the spirit of the invention or the scope of the appended claims.

We claim:
1. In the production of a imprinting device comprising a frame member having a window therein, a thin film of impression conforming material secured across said window, and a coating of wet ink adhered to one surface of the film, the method comprising the steps of:
   a. depositing a thin resinous film forming coating containing a resinous elastomer and diatomaceous earth filler having ink-absorbing and film flattening properties, said coating having sufficient amounts of said resinous elastomer and filler to form a thin, flat film of impression conforming material which is sufficiently thin and flexible to conform to the impressions and ridges of relief patterns, including fingerprints in a liquid solvent on a releasable web;

b. drying the resinous coating to form said thin flat film of impression conforming material having a thickness of about 0.0001 to 0.001 in.;

c. applying a coating of slow drying wet ink to the exposed surface of the releasable web supported film, so said ink remains wet but not wet enough to disturb the quality of the print;

d. removing the releasable web from the film; and e. bonding the film to the frame member with the inked surface of the film facing through said window.

2. The method according to claim 1 wherein:

a. the resinous film forming coating has a thickness of about 0.0001 to 0.001 inches.

3. The method according to claim 2 wherein:

a. the amount of resinous elastomer comprises about 5 to 50 parts per hundred parts by weight of the liquid solvent; and b. the amount of filler comprises 5 to 40 parts per hundred parts by weight of the resinous elastomer.

4. The method according to claim 3 wherein:

a. the amount of resinous elastomer comprises 15 parts per hundred parts by weight of the liquid solvent.

5. The method according to claim 4 wherein:

a. the resinous elastomer is polyurethane.

6. The method according to claim 5 wherein:

a. the liquid solvent comprises tetrahydrofuran and acetone in the ratio of 3 parts tetrahydrofuran to 1 part acetone by weight.

* * * * *